United States Patent [19]

Umezawa et al.

[11] 4,349,666
[45] Sep. 14, 1982

[54] PROCESS FOR THE PRODUCTION OF KANOMYCIN B DERIVATIVES AND PRODUCTS OBTAINED THEREFROM

[75] Inventors: Hamao Umezawa; Sumio Umezawa, both of Tokyo; Tsutomu Tsuchiya, Yokohama; Toshiaki Miyake, Kawasaki, all of Japan

[73] Assignee: Zaidan Hojin Biseibutsu Kagaku Kenkyu Kai, Tokyo, Japan

[21] Appl. No.: 196,586

[22] Filed: Oct. 14, 1980

[30] Foreign Application Priority Data

Oct. 30, 1979 [JP] Japan .................................. 54-139262

[51] Int. Cl.$^3$ ............................................ C07H 15/22
[52] U.S. Cl. .................................. 536/13.8; 424/180; 536/13.7
[58] Field of Search .......................................... 536/10

[56] References Cited

U.S. PATENT DOCUMENTS

| | | | |
|---|---|---|---|
| Re.28,647 | 12/1975 | Umezawa et al. ..................... | 536/10 |
| 3,929,762 | 12/1975 | Umezawa et al. ..................... | 536/10 |
| 4,125,706 | 11/1978 | Umezawa et al. ..................... | 536/10 |
| 4,156,078 | 5/1979 | Umezawa et al. ..................... | 536/10 |
| 4,195,170 | 3/1980 | Umezawa et al. ..................... | 536/10 |

Primary Examiner—Johnnie R. Brown
Attorney, Agent, or Firm—Larson and Taylor

[57] ABSTRACT

3'-Deoxykanamycin B, namely tobramycin is produced in an improved yield with a reduced reaction time under moderate reaction conditions, starting from a penta-N-protected 3'-mono-O-alkyl-, aralkyl- or arylsulfonylated derivative of kanamycin B in which all the 1, 3, 2' and 3''-amino groups and possibly the 6'-amino group have been protected by an arylsulfonyl group, especially tosyl group; the 3'-hydroxyl group of kanamycin B has been alkyl-, aralkyl- or arylsulfonylated; the 4''- and 6''-hydroxyl groups have been blocked with a di-valent hydroxyl-protecting group; and possibly the 4'-hydroxyl group and 6'-amino group have been blocked by being converted into the form of a 4', 6'-cyclic carbamate formed between the 4'-hydroxyl group and the 6'-amino group, by subjecting to a process essentially comprising reaction of said protected kanamycin B derivative with a metal halide for a reaction time of 30 min. to 2 hours at a reaction temperature of 0° C.~150° C. to produce the corresponding 3'-halo compound, reductive replacement of the 3'-halo group by hydrogen and deprotection.

9 Claims, No Drawings

PROCESS FOR THE PRODUCTION OF KANOMYCIN B DERIVATIVES AND PRODUCTS OBTAINED THEREFROM

BACKGROUND OF THE INVENTION

This invention relates to new processes for the production of tobramycin, namely 3'-deoxykanamycin B from a protected derivative of kanamycin B.

DESCRIPTION OF THE PRIOR ART

We already reported a process for the synthesis of 3'-deoxykanamycin B starting from kanamycin B (see Japanese Patent Pre-publication "Kokai" No. 80038/74 and U.S. Pat. No. 3,929,762). According to this process, all the five amino groups of kanamycin B are protected with an amino-protecting group which is either of alkyloxycarbonyl, aralkyloxycarbonyl or aryloxycarbonyl type, for example, ethoxycarbonyl or benzyloxycarbonyl group or of Schiff base type, for example, salicylidene group, and the 4''- and 6''-hydroxyl groups of kanamycin B are protected with a divalent hydroxyl-protecting group, for example, cyclohexylidene or tetrahydropyranylidene group. The protected derivative so obtained is then reacted at a temperature below 100° C. with an alkylsulfonyl halide, aralkylsulfonyl halide or arylsulfonyl halide or a corresponding sulfonic anhydride in a proportion of 1.5 mol or less in a basic organic solvent, preferably in dry pyridine, whereby the 3'-hydroxyl group of the kanamycin B derivative is selectively sulfonylated substantially without accompanying the sulfonylation of the 4'-hydroxyl group. The 3'-mono-O-sulfonylation product so obtained is reacted with a solution of 50% or more sodium or lithium bromide or iodide in an aprotic organic solvent to convert the 3'-sulfonyloxy group into the bromo or iodo radical, which is then reductively replaced by hydrogen atom to produce a 3'-deoxy derivative of kanamycin B. The latter is further subjected to the deprotection to remove the residual protecting group, affording 3'-deoxykanamycin B.

However, the known process as above has the drawbacks that it takes about 24 hours or a longer time to accomplish the conversion of the 3'-O-sulfonylated compound into the 3'-halo compound even when this conversion reaction is carried out by reacting with an alkali metal bromide or iodide at a concentration of 50% or more at a temperature of about 100° C. or higher, with the result that undesirable by-products are formed and/or degradation of the desired product takes place. It has been found that when said conversion is conducted under milder reaction conditions or at a lower concentration of the alkali metal halide than 50%, then the reaction proceeds too slowly to make the process suitable for practice.

We have made further studies to obviate the above-mentioned drawbacks, and we have now found that when an arylsulfonyl group, especially tosyl group is selected as the amino-protecting group for use in the N-protection of kanamycin B from amongst the known amino-protecting groups of the sulfonyl type such as alkylsulfonyl groups, aralkylsulfonyl groups and arylsulfonyl groups in place of the alkyloxycarbonyl groups, aralkyloxycarbonyl groups or aryloxycarbonyl groups which were employed as the amino-protecting group in the process of the above-mentioned Japanese patent pre-publication "Kokai" No. 80038/74 or U.S. Pat. No. 3,929,762, it is not only feasible to achieve the preferential sulfonylation of the 3'-hydroxyl group of kanamycin B likewise by reacting with the sulfonylation agent in the same manner as described in the specification of the Japanese patent pre-publication "Kokai" No. 80038/74 or U.S. Pat. No. 3,929,762, but also it is possible to accomplish the reaction of the resulting 3'-O-sulfonylation product with an alkali metal or other metal iodide or bromide in a reduced reaction time of 30 minutes to 2 hours at a reaction temperature of 0° C. to 150° C. for finishing the substitutive 3'-bromination or 3'-iodination even at a lower concentration of 3~50% of the metal halide employed, so that a considerable reduction in the reaction time required for the 3'-halogenation can be attained, and besides that the use of the arylsulfonyl group as the amino-protecting group makes it possible to convert the 3'-O-sulfonylated kanamycin B derivative into the corresponding 3'-chloro derivative by reacting with an alkali metal or other metal chloride, contrary to our experiences previously obtained in the process of the U.S. Pat. No. 3,929,762. On the basis of these our findings is completed this invention.

Further, we already developed and claimed a process for the synthesis of 3',4'-dideoxykanamycin B from kanamycin B (Japanese Patent Publication Nos. 7595/75 and 46110/76 and U.S. Pat. No. 3,753,973) and an alternative process for the same (U.K. Patent No. 1,555,661 or U.S. Pat. No. 4,156,078). In the latter process, all the five amino groups of kanamycin B are protected with an amino-protecting group of the same sulfonyl type as mentioned hereinbefore, and the 4''- and 6''-hydroxyl groups are protected with a di-valent hydroxyl-protecting group. The protected derivative so obtained is then reacted with an alkyl-, aryl- or aralkylsulfonic acid halide, especially benzylsulfonyl chloride in dry pyridine at a relatively low temperature of −30° C. ~ +30° C. to benzyl sulfonylate both the 3'- and 4'-hydroxyl groups, followed by the reaction of the resultant 3',4'-disulfonic ester product with sodium iodide for a time of 30 min. to 3 hours at a temperature of 50° to 150° C. to effect the de-sulfonyloxylation and produce a 3',4'-eno derivative (the 3',4'-unsaturated derivative). The 3',4'-unsaturated bond of said eno derivative is hydrogenated to give a protected derivative of 3',4'-dideoxykanamycin B which is then treated with metallic sodium in liquid ammonia or the like to remove the residual amino-protecting sulfonyl groups, resulting in the production of 3',4'-dideoxykanamycin B. In the study of the process of the above-mentioned U.K. patent No. 1,555,661, we found that when a protected kanamycin B derivative having all the five amino groups protected with the amino-protecting group of the sulfonyl type and having the 4''- and 6''-hydroxyl groups blocked with a di-valent hydroxyl-protecting group was reacted with 2 molar proportion of benzylsulfonyl chloride in pyridine at a relatively low temperature of −30° to 30° C. overnight, both the 3'- and 4'-hydroxyl groups of the kanamycin B compound could be benzylsulfonylated to give the 3',4'-di-O-sulfonic acid ester. While, we have now discovered that when the similarly N-sulfonylated and 4'',6''-O-protected kanamycin B derivative is reacted with about 1 molar proportion or more of an alkyl-, aryl- or aralkylsulfonic acid halide in dry pyridine at a temperature of −40° C. to about 100° C. for a reaction time of 30 minutes to 24 hours, the 3'-hydroxyl group of the kanamycin B compound can preferentially be alkyl-, aryl- or aralkylsulfonylated with involving no or a little sulfonylation of the 4'-hydroxyl group, affording the corresponding 3'-mono-O-sulfonylated kanamycin B derivative as the main sulfonylation product.

DETAILED DESCRIPTION OF THE INVENTION

A principal object of this invention is to provide a new processes for the production of tobramycin (3'-deoxykanamycin B) starting from an amino-protected and 3'-mono-O-sulfonylated derivative kanamycin B.

Other objects and advantages of the invention will become apparent from the following description.

According to a first aspect of this invention, there is provided a process for the production of tobramycin of the formula

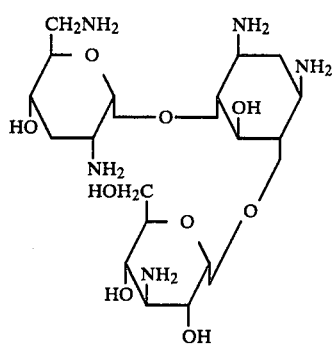

which comprises the steps of:

reacting a 1, 3, 2', 6', 3"-N-protected, 4",6"—O—-protected and 3'-O-sulfonylated derivative of kanamycin B of the general formula (I)

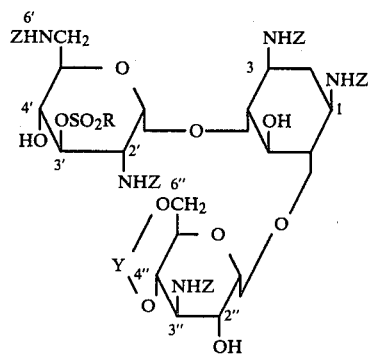

wherein R is an alkyl group, particularly an alkyl group of 1~4 carbon atoms, an aralkyl group, particularly a phenylalkyl group of 7~11 carbon atoms, especially benzyl group or an aryl group, especially phenyl group, Y is an alkylidene group of 1~6 carbon atoms, a cycloalkylidene group of 3~6 carbon atoms, an aralkylidene group or tetrahydropyranylidene group as a divalent hydroxyl-protecting group and each Z is an arylsulfonyl group, particularly tosyl group as the amino-protecting group, with a metal halide of the formula (II)

MX   (II)

wherein M is a metal, particularly an alkali metal and X is iodine, chlorine or bromine, in an organic solvent at a temperature of 50°~150° C. for a time of 30 minutes to 2 hours to produce the 3'-halogenated compound of the formula (III)

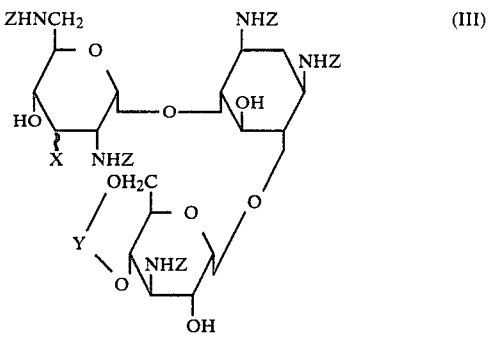

wherein X, Y and Z are as defined above, reducing the 3'-halo group (X) of the compound (III) in a known manner to replace the 3'-halo group by hydrogen and to produce the corresponding 3'-deoxykanamycin B compound, and removing from the latter the remaining amino-protecting groups (Z) and the remaining hydroxyl-protecting group (Y) in a known manner.

The process of this invention consists in a first application to the semi-synthetic production of tobramycin from kanamycin B of our own discovery that a compound comprising a 2-amino-2-deoxy-α-D-glucopyranoside moiety having the amino group arylsulfonylated (especially, tosylated) and having the 3-hydroxyl group alkyl-, aryl- or aralkylsulfonylated is capable of being readily halogenated (i.e. chlorinated, brominated or iodinated) at the 3-position to give the 3-halo derivative, and that this 3-halo derivative can undergo a conventional reductive substitution with hydrogen to achieve the 3-deoxygenation, giving the corresponding 3-deoxy derivative. This our discovery is novel and the first application of our discovery in this invention is original, as far as we are aware of.

The preparation of the N,O-protected and 3'-mono—O—sulfonylated derivative of kanamycin B of the above formula (I) which is employed as the starting material in the present process may be made in the following way.

Thus, kanamycin B is used as the initial material, and all its five amino groups are arylsulfonylated and then the 4"- and 6"-hydroxyl groups are protected with a di-valent hydroxyl-protecting group to prepare the penta-N-arylsulfonylated and 4",6"-O-protected derivative of kanamycin B, according to the procedures as described in U.K. patent No. 1,555,661 and also in the "Carbohydrate Research" 49, 141 (1976).

This protected derivative of kanamycin B is dissolved in an organic solvent, for example, in dry pyridine and then reacted with an alkyl-, aryl- or aralkyl-sulfonic acid halide of the formula:

RSO$_2$X wherein R is a lower alkyl group, an aryl group or an aralkyl group, or an anhydride thereof, particularly an arylsulfonic acid halide or anhydride in such a way that the selective sulfonylation of the 3'-hydroxyl group is effected to give the compound (I). As the organic solvent used for the selective 3'-mono-O-sulfonylation, pyridine is most suitable, although there may be used any aprotic neutral solvent which generally includes basic organic solvents such as picoline, N-alkylmorpholine or triethylamine and in which said protected derivative may wholly or partially dissolve. Examples of the solvent for this purpose include methylformamide, dimethylacetamide, dimethylsulfoxide, tetrahydrofuran, dioxane, ethyl ether, chloroform, benzene and sulforane. The sulfonic acid halide or the corresponding anhydride is suitably used in a proportion of 1 to 5 moles per mol of the protected derivative of kanamycin B.

Preferred examples of the sulfonylating agent (RSO$_2$X) for present use include tosyl chloride, p-toluenesulfonic anhydride, benzylsulfonyl chloride and methanesulfonyl chloride. The 3'-mono-O-sulfonylation may be carried out at a temperature in the range from −40° C. to +100° C., preferably from −20° C. to +25° C. for a period of time ranging from 30 minutes to 24 hours.

The 3'-mono-O-sulfonylation of the kanamycin B compound can occasionally be accompanied by more or less side-reactions such as sulfonylation of the 4'-hydroxyl group as well as sulfonylation of the 2''-hydroxyl group. However, the 3',4'-di-O-sulfonylated derivative and the 3',4',2''-tri-O-sulfonylated derivative so by-produced are useful as a starting material in the synthesis of 3', 4'-dideoxykanamycin B (i.e. dibekacin) according to the method of U.S. Pat. No. 3,753,973, and in this sense, the process of this invention provides a new route for the preparation of tobramycin in which there is not formed any by-product which is useless in any way.

In carrying out the first aspect process of the invention, the starting protected kanamycin B compound (I) is reacted with a metal halide of the above formula (II) in which the halogen X may be chlorine, bromine or iodine but cannot be fluorine and the metal M includes an alkali metal, an alkaline earth metal and a heavy metal, to effect the 3'-halogenation. In practice, lithium chloride, bromide and iodide and sodium iodide are suitably used as the metal halide. The metal halide is generally used in an amount of 1 mol to 100 moles, especially 2~10 moles per mole of the starting compound (I).

The reaction (the 3'-halogenation) is usually carried out in an organic solvent in which both of the reactants can be dissolved. Suitable examples of the solvent include dimethylformamide, hexamethylphosphoric triamide and dimethylsulfoxide, or a mixture thereof with an aprotic neutral organic solvent as mentioned hereinbefore for the 3'-mono-O-sulfonylation. The reaction is effected at a temperature of 0°~150° C. for a period of 30 minutes to about 2 hours.

The 3'-halogenated compound of the above formula (III) so obtained is then subjected to the reductive dehalogenation at the 3'-position by a conventional technique, for example, catalytic hydrogenation with hydrogen or reduction with a halogen-reducing agent such as an trialkyltin hydride, for example, tributyltin hydride or treatment with an alkali metal in liquid ammonia. There is thus produced the protected derivative of 3'-deoxykanamycin B in which the 3'-halo group has been replaced by hydrogen.

The amino-protecting groups of arylsulfonyl type which are remaining in the protected derivative of 3'-deoxykanamycin B so produced can be removed from the latter by a known deprotecting method, typically by treatment with a metal (preferably metallic sodium) in liquid ammonia as described in our U.K. Pat. No. 1,555,661. The divalent 4'',6''-O-protecting group (i.e. alkylidene, cycloalkylidene, aralkylidene, or tetrahydropyranylidene group) which will generally remain in said protected derivative can be removed in a known manner by acid hydrolysis to afford the desired product, 3'-deoxykanamycin B, that is, tobramycin.

In an alternative way, if the 3'-halogenated compound (III) is directly treated with a metal or metal amalgam (notably sodium or sodium amalgam) in liquid ammonia, the removal of the amino-protecting groups (Z) may take place concurrently with the reductive replacement of the 3'-halo group (X) by hydrogen. Then, the partially deprotected 3'-deoxykanamycin B derivative so obtained can subsequently be subjected to an acid hydrolysis to remove the divalent hydroxyl-protecting group (Y), affording the desired 3'-deoxykanamycin B.

According to the first aspect process of this invention, the 3'-mono-O-sulfonylation for preparing the starting compound (I) may possibly by associated to some extent with the side-reaction by which the 4'-hydroxyl group is sulfonylated, as stated hereinabove. This possibility, however, will be perfectly avoided by selective protection of the 4'-hydroxyl group. In the course of our development of a process for the synthesis of 3',4'-dideoxykanamycin A from kanamycin A (see our copending Japanese Patent Application No. 11402/79, copending U.S. patent application Ser. No. 114,779, now Pat. No. 4,298,727; Belgian patent No. 881,251), we have discovered that the 4'-hydroxyl group of kanamycin A can be blocked by treating with sodium hydride such a 4'-O-unprotected, 6'-N-protected derivative of kanamycin A having the 6'-amino group protected with an alkyloxycarbonyl, aralkyloxycarbonyl or aryloxycarbonyl group, so as to form a 4',6'-cyclic carbamate derivative.

We have now found that the above procedure of protecting the 4'-hydroxyl group of kanamycin A by converting into the form of the 4', 6'-cyclic carbamate can also be applied to a 4'-O-unprotected, 6'-N-protected derivative of kanamycin B, and we have succeeded in preparation of a protected 4',6'-carbamate dirivative of kanamycin B suitable as the starting material for the production of tobramycin.

According to a second aspect of this invention, therefore, there is provided a process for the production of tobramycin, which comprises the steps of:
reacting a 1,3,2',3''-N-protected, 4'',6''-O-protected, 6'-N:4'-O-carbonylated and 3'-O-sulfonylated derivative of kanamycin B of the general formula (IV)

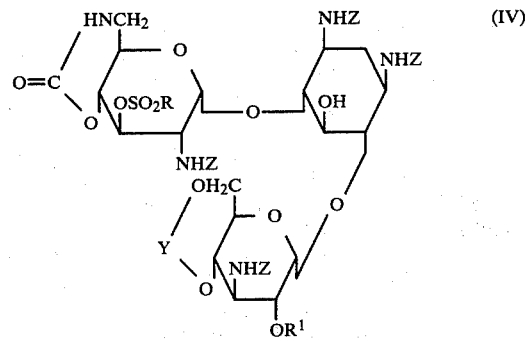

wherein R is an alkyl, aralkyl or aryl group, R¹ is either hydrogen atom or an alkylsulfonyl, aralkylsulfonyl or arylsulfonyl group same as the group —SO₂R shown in the formula, Y is an alkylidene group of 1~6 carbon atoms, a cycloalkylidene group fo 3~6 carbon atoms, an aralkylidene group or tetrahydropyranylidene group as the divalent hydroxyl-protecting group, and each Z is an arylsulfonyl group, particularly tosyl group as the amino-protecting group, with a metal halide of the formula (II)

MX    (II)

wherein M is a metal, particularly an alkali metal and X is iodine, chlorine or bromine, in an organic solvent at a temperature of 50°~150° C. for a time of 30 minutes to 2 hours to produce the 3'-halogenated compound of the formula (V)

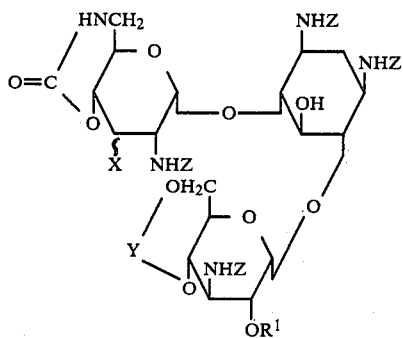

wherein X, Y, Z and R¹ are as defined above. reducing the 3'-halo group of the compound (V) in a known manner to replace the 3'-halo group by hydrogen and to produce the corresponding 3'-deoxykanamycin B compound which is still in the form of the 4', 6'-cyclic carbamate, and treating the latter in a known manner to fission the 4', 6'-cyclic carbamate ring and to remove the remaining amino-protecting groups (Z) and the hydroxyl-protecting group (Y) therefrom.

The protected derivative of kanamycin B in the form of the 4', 6'-carbamate according to the above formula (IV) which is used as the starting material in the second aspect process of this invention can be prepared by the following procedures, the particulars of which are illustrated by Example 3 hereinafter:

Kanamycin B is at first subjected to a known method for the selective protection of the 6'-amino group with an alkoxycarbonyl, aryloxycarbonyl or aralkyloxycarbonyl group. Since the 6'-amino group is more reactive than the other amino groups of kanamycin B, an amino-protecting group of alkoxycarbonyl, aryloxycarbonyl or aralkyloxycarbonyl type can preferentially be introduced into the 6'-amino group, for example, by reacting kanamycin B (free base) in water at a temperature of 0°~10° C. with 0.5 to 3 molar proportion of an alkoxycarbonyl-, aryloxycarbonylor aralkyloxycarbonyl-chloroformate according to the method of Kawaguchi et al. as described in the "Journal of Antibiotics", 25, 695~708, 1972 or U.S. Pat. No. 3,781,268, for example. The reaction conditions to this end may be similar to those used for the preparation of 6'-N-benzyloxycarbonylkanamycin A according to the method of Example 1 of U.S. Pat. No. 3,925,353. Our experiments have shown that the 6'-N-protected derivative of kanamycin B is obtained in a high yeild when the 6'-amino group of kanamycin B is selectively protected either by the method of Nagabhushan et al. as described in U.S. Pat. No. 4,136,254 or by a method of our co-pending Japanese patent application No. 138402/78 (corresponding to our co-pending U.S. patent application Ser. No. 90,591, now U.S. Pat. No. 4,297,485; co-pending U.K. patent application No. 7938894; and Belgian Patent No. 879,925). According to the former method, kanamycin B is first reacted with a divalent transition metal cation, for example, copper (II), nickel (II) or cobalt (II) cation to form such a metal complex or chelate of kanamycin B in which the 1- and 3''-amino groups have been blocked by complexing with the divalent metal cation, and the kanamycin B-metal complex so formed is then reacted with an amino-protecting reagent to protect the 6'-amino group, followed by removing the metal cation from said complex, for example, by treatment with hydrogen sulfide or aqueous ammonia. According to the latter method (of Belgian patent No. 879,925), the 6'-N-protected derivative is prepared in the same way as the former method, except that zinc metal is used instead of the divalent transition metal.

The 6'-N-alkoxycarbonyl-, aryloxycarbonyl- or aralkyloxycarbonyl-kanamycin B thus obtained is reacted with 4 moles or more of an arylsulfonyl chloride in an organic solvent to give the corresponding 6'-N-alkoxy-, aryloxy- or aralkyloxycarbonyl-1,3,2',3''-tetra-N-arylsulfonylkanamycin B derivative. The latter can conveniently be prepared, for example, by reacting said 6'-N-protected kanamycin B with a substantially stoichiometic quantity of an arylsulfonyl chloride, especially tosyl chloride in an organic solvent such as dioxane at a temperature between −30° C. and +50° C. in the presence of an alkali such as sodium carbonate.

Subsequently, the 4''- and 6''-hydroxyl groups of the tetra-N-arylsulfonylated kanamycin B compound as above are protected with a divalent hydroxyl-protecting group (Y) by conversion into the form of acetal or ketal as described hereinbefore or as described also in Japanese Patent Publication No. 7595/75 or U.S. Pat. No. 3,929,762, for instance. Specific examples of the divalent hydroxyl-protecting group include an alkylidene group containing 1 to 6 carbon atoms such as methylene, ethylidene and isopropylidene; a cycloalkylidene group containing 3 to 6 carbon atoms, notably cyclohexylidene; an aralkylidene group, notably benzylidene; and tetrahydro-4-pyranylidene group. Thus, the protection of the 4'',6''-hydroxyl groups may preferably be effected by reaction at a relatively low temperature of e.g. 10°~80° C. with formaldehyde or 2,2-dimethoxypropane for the alkylidenation, benzaldehyde for the aralkylidenation or 1,1-dimethoxycyclohexane for the cycloalkylidenation in the presence of an acid catalyst such as p-tolenesulfonic acid or sulfuric acid in a known manner as described in U.S. Pat. No. 3,929,762.

The 4'',6''-O-protected derivative so produced may be dissolved in an appropriate organic solvent, for example, dimethylformamide and reacted with a basic reagent such as sodium hydride to form the corresponding 4',6'-cyclic carbamate derivative in a known manner as described in "Journal of Antibiotics" 25, No. 12, 741–742, 1972 or U.S. Pat. Nos. 3,925,354 or 4,125,706. The method for the conversion of the 4'',6''-O-protected derivative into the 4',6'-cyclic carbamate form is disclosed in detail also in our Japanese Patent Publication No. 24415/78 and Japanese Patent-Pre-publication ("Kokai") Nos. 80039/74, 101355/74, 127046/76 and 23043/77.

The 4′,6′-cyclic carbamate derivative so obtained is then reacted with an alkyl-, aralkyl- or arylsulfonic halide or anhydride of the formula:

$$RSO_2X \text{ or } (RSO_2)_2O \qquad (VII)$$

wherein R and X are as defined hereinabove, in such a way as described in U.K. Patent No. 1,555,661. In this way, the 3′-hydroxyl group and possibly the 2″-hydroxyl group of the carbamate derivative are sulfonylated to form such a 3′-mono-O-sulfonylated kanamycin B derivative of the above formula (IV) in which $R^1$ is hydrogen, either alone or in association with such a 3′,2″-di-O-sulfonylated kanamycin B derivative of the formula (IV) in which $R^1$ is the group —$SO_2R$.

The mixture of the 3′-mono-O-sulfonylated kanamycin B derivative and the 3′,2″-di-O-sulfonylated kanamycin B derivative prepared in the above way may directly be used as such in the second aspect process of this invention or may, if desired, be separated by a column chromatography on silica gel developed with chloroform-methyl ethyl ketone (1:2), so that the 3′-mono-O-sulfonylated kanamycin B derivative is isolated from the 3′,2″-di-O-sulfonylated kanamycin B derivative and each of these products so isolated is used as the starting material (IV) in the second aspect process of this invention.

In carrying out the second aspect process of this invention, the starting kanamycin B derivative of the formula (IV) wherein $R^1$ is a hydrogen atom and the starting kanamycin B derivative of the formula (IV) where $R^1$ is the sulfonyl group —$SO_2R$, either alone or in mixture, is reacted with a metal halide of the formula (II) in the same manner as hereinbefore described with respect to the first aspect process of this invention, so that the 3′-**sulfonyloxy group is halogenated. The 3′-halogenated product so obtained is then reduced in the same manner as in the first aspect process of this invention to replace the 3′-halo group by hydrogen, giving the 3′-deoxykanamycin B compound which is corresponding to such a compound of the formula (V) but where the group X has been converted into the hydrogen atom. When the protected 3′-deoxykanamycin B compound so obtained is then subjected to the known deprotecting technique as described hereinbefore in respect of the first aspect process of this invention, there is produced the desired 3′-deoxykanamycin B, that is, tobramycin. Even when the 3′,2″-di-O-sulfonylated kanamycin B compound is used as the starting material (IV) in the present process, the 2″-O-sulfonyl group can be removed readily in the later deprotecting stage of the present process, for example, by the treatment with metallic sodium in liquid ammonia, so that the desired tobramycin is given in a high yield.

Either according to the first aspect process or according to the second aspect process of this invention, the final product tobramycin can be obtained in an overall yield of about 30% as calculated from the initial kanamycin B, and this provides some improvement in the overall yield of tobramycin, in comparison with the prior method of the above-mentioned Japanese patent pre-publication "Kokai" No. 80038/74 or U.S. Pat. No. 3,929,762 where the overall yield of tobramycin is usually in the order of about 25% as calculated from the initial kanamycin B. Besides, it is to be noticed that the processes of this invention need only a time of 30 minutes to at most 2 hours in the 3′-halogenation step, whereas the prior method of the U.S. Pat. No. 3,929,762 takes 24 hours or more for its 3′-halogenation stage.

In the first and second aspect processes of this invention, it is possible that the 3′-halo group of the 3′-halogenated product of the formula (III) or (V) is reductively replaced by hydrogen by treating with metallic sodium in liquid ammonia, when the removal of the amino-protecting sulfonyl groups (Z) and possibly the removal of the 2″-O-sulfonyl group (when present) are effected concurrently, so that the number of the operations required for the step for removing all the protective groups from the intermediate compound (III) or (V) is reduced, as compared to that required in the prior method of the U.S. Pat. No. 3,929,762. Moreover, the operations necessary in the respective steps of the present processes are simplier and more facile, making the processes of this invention suitable for commercial production of tobramycin. It is very convenient in the processes of this invention if the steps of reducing the 3′-halo group and of removing the protective groups are carried out in such a way that the 3′-halo compound (III) or (V) is reacted with metal sodium in liquid ammonia to effect concurrently the reduction of the 3′-halo group (X) into hydrogen and the removal of the amino-protecting arylsulfonyl groups (Z), and the reaction mixture in the liquid ammonia is admixed with methanol and then distilled to remove the residual ammonia, the residue is dissolved in water and heated to effect the fission of the 4′,6′-cyclic carbamate ring which is remaining when the compound (V) is employed, and the resulting solution in water is admixed and neutralized with a strongly acidic cation-exchange resin containing sulfonic functions to effect the removal of the divalent hydroxyl-protecting group (Y), giving tobramycin.

The first aspect process of this invention provides as the new intermediate compound which is useful for the production of tobramycin, the 1,3,2′,6′,3″-penta-N-sulfonylated, 4″,6″-O-protected and 3′-halogenated kanamycin B compound of the formula (III)

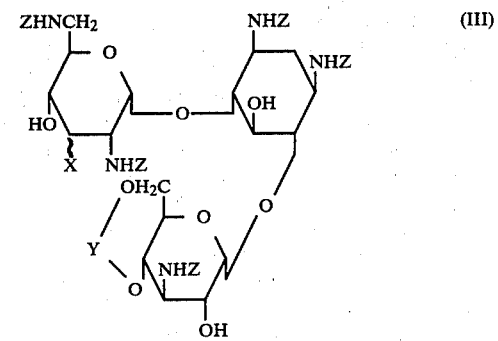

wherein X is a halo group, Y is an alkylidene group of 1~6 carbon atoms, a cycloalkylidene group of 3~6 carbon atoms, an aralkylidene group or tetrahydropyranylidene group as a divalent hydroxyl-protecting group and each Z is an arylsulfonyl group, particularly tosyl group as the amino-protecting group.

A particular example of the above intermediate compound of the formula (III) is 4″,6″-O-cyclohexylidene-3′-deoxy-3′-iodo-1,3,2′,6′,3″-penta-N-tosylkanamycin B.

The second aspect process of this invention provides likewise as the new and useful intermediate compound the 1,3,2′,3″-tetra-N-sulfonylated, 4″,6″—O— protected, 6'-N:4'-O-carbonylated and 3'-halogenated kanamycin B compound of the formula (V)

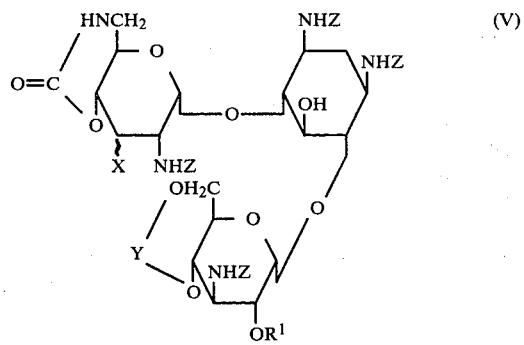

wherein X is a halo group, $R^1$ is either hydrogen atom or an alkylsulfonyl, aralkylsulfonyl or arylsulfonyl group same as the group —$SO_2R$ shown in the formula, Y is an alkylidene group of 1~6 carbon atoms, a cycloalkylidene group of 3~6 carbon atoms, an aralkylidene group or tetrahydropyranylidene group as the divalent hydroxy-protecting group, and each Z is an arylsulfonyl group, particularly tosyl group as the amino-protecting group.

Particular examples of the intermediate compound of the formula (V) are:
(1) 6'-N:4'-O-carbonyl-4'',6''-O-cyclohexylidene-3'-deoxy-3'-iodo-1,3,2',3''-tetra-N-tosylkanamycin B;
(2) 2''-O-benzylsulfonyl-6'-N:4'-O-carbonyl-3'-chloro-4'',6''-O-cyclohexylidene-3'-deoxy-1,3,2',3''-tetra-N-tosylkanamycin B;
(3) 6'-N:4'-O-carbonyl-3'-chloro-4'',6''-O-cyclohexylidene-3'-deoxy-1,3,2',3''-tetra-N-tosylkanamycin B.

This invention is further illustrated but not limited by the following Examples.

EXAMPLE 1

(i) Preparation of 3'-O-benzylsulfonyl-4'',6''-O-cyclohexylidene-1,3,2',6',3''-penta-N-tosylkanamycin B 4'',6''-Cyclohexylidene-1,3,2',6',3''-penta-N-tosylkanamycin B (1.56 g) (prepared as described in the "Carbohydrate Research" 49, 141~151, 1976) was dissolved in 31 ml of dry pyridine, and the solution was cooled to −20° C. and admixed with 225 mg benzylsulfonyl chloride. The mixture was allowed to stand at −20° C. for 21 hours to effect the 3'-mono-O-benzylsulfonylation. The reaction solution was admixed with 0.11 ml of water and was concentrated to a syrup, which was taken up into a volume of chloroform to give 100 ml of the solution in chloroform. The solution was washed with 5% aqueous sodium bicarbonate and then with water, concentrated to dryness and dried over anhydrous sodium sulfate to afford 1.78 g of a solid. The solid was chromatographed on silica gel developed with chloroform-methyl ethyl ketone (1:1 by volume) to give 391 mg (23%) of a purified solid as the title compound. $[\alpha]_D^{25} = -2°$ (c=1 in chloroform).

Elemental Analysis

Found: C 53.20; H 5.51; N 4.52; S 12.71%. Calcd. for $C_{66}H_{81}N_5O_{22}S_6$: C 53.25; H 5.48; N 4.70; S 12.92%.

(ii) Preparation of 3'-O-tosyl-4'',6''-O-cyclohexylidene-1,3,2',6',3''-penta-N-tosylkanamycin B The 4'',6''-cyclohexylidene-1,3,2',6',3''-penta-N-tosylkanamycin B (104 mg) was dissolved in 2 ml of dry pyridine, to which was then added 74.6 mg of tosyl chloride. The mixture was allowed to stand at 70° C. for 12 hours to perform the 3'-mono-O-tosylation. The resultant reaction solution was subsequently treated in the same way as in the above procedure (i) to give 98.6 mg (85%) of a solid of the tital compound. $[\alpha]_D^{25} = -3°$ (c=1 in chloroform).

EXAMPLE 2

Synthesis of tobramycin (a) Preparation of 4'',6''-O-cyclohexylidene-3'-deoxy-3-iodo-1,3,2',6',3''-penta-N-tosylkanamycin B (i) 64.8 mg of the product obtained in the above Example 1(i) was dissolved in 1.3 ml of dimethylformamide, followed by addition of 650 mg of sodium iodide and agitation at 100° C. for one hour to effect the 3'-iodination. Thereafter, the reaction solution was allowed to stand at ambient temperature to solidify it, and the solid was suspended in 20 ml of chloroform. The suspension was washed successfully with water, 10% aqueous sodium thiosulfate and water, then concentrated to a small volume and subjected to azeotropic distillation with xylene. The residue obtained was dissolved in chloroform, dried over anhydrous sodium sulfate and evaporated to afford 62.8 mg of a crude solid. The solid was purified by column chromatography on silica gel developed with a mixed solvent of benzene/ethyl acetate (2:3) to give 51.2 mg (83%) of the title compound as colorless solid. $[\alpha]_D^{25} = +11°$ (c=1 in chloroform).

Elemental Analysis

Found: C 49.06; H 5.16; N 4.85%. Calcd. for $C_{59}H_{74}N_5O_{19}S_5I$: C 49.18; H 5.18; N 4.69%.

(ii) 107 mg of the product obtained in the above Example 1(ii) was dissolved in 2 ml of dimethylformamide, to which was then added 1.1 g of sodium iodide and the mixture was agitated at 100° C. for 40 minutes to effect the 3'-iodination. The reaction solution was subsequently treated following the same procedure as in Example 2(i) to yield 93.6 mg (90%) of the title compound.

(b) Preparation of 4'',6''-O-cyclohexylidene-3'-deoxy-1,3,2',6',3''-penta-N-tosylkanamycin B 51.1 mg of the product obtained in the step (a) above of this Example 2 was dissolved in 1 ml of dioxane, to which was then added 0.1 ml of tri-n-butyltin hydride followed by 5 ml of α,α'-azobisisobutyronitrile (as catalyst). The resultant mixture was allowed to stand at 80° C. for 2 hours under nitrogen atmosphere to accomplish the reductive replacement of the 3'-iodo group by hydrogen. The reaction solution was then concentrated to a syrup, which was admixed with ethyl ether to precipitate a solid. The solid was filtered off, washed with ethyl ether and dried to give 33 mg (84%) of the title compound. $[\alpha]_D^{25} = +10°$ (c=0.5 in dimethylformamide).

(c) Production of 3'-deoxykanamycin B (tobramycin)

47.9 mg of the product from the step (b) above of this Example 2 was dissolved in 5 ml of liquid ammonia at a temperature of −50° C., 50 mg of sodium metal was added to the resulting solution and the mixture was agitated at the same temperature for one hour to effect the removal of the amino-protecting groups (tosyl group). The reaction solution obtained was admixed with methanol and stirred at ambient temperature and then the ammonia was distilled off under reduced pressure. The residue was taken up in water, and the solution was neutralized with addition of a strongly acidic ion-exchange resin, Dowex 50 W×2 (H form) (a product of Dow Chemical Co., U.S.A.), resulting in the removal of the 4″,6″-O-cyclohexylidene group. The resin was charged into a column, which was then eluted with 1 N aqueous ammonia. The eluate was collected in 1 ml-fractions and those fractions which were positive to ninhydrin reaction were combined together and concentrated to dryness to afford 25.9 mg of a crude solid of 3′-deoxykanamycin B.

This solid was dissolved in water and the solution was passed through a column of CM-Sephadex C-25 ($NH_4^+$ form) (a product of Pharmacia Fine Chemicals Co., Sweden). The column was then subjected to gradient elution with 0→0.15 N aqueous ammonia. Those fractions containing the desired product were combined together and concentrated to dryness to yield 12.0 mg (62%) of 3′-deoxykanamycin B monocarbonate. $[\alpha]_D^{25} = +125°$ (c=1 in water).

Elemental Analysis

Found: C 42.95; H 7.62; N 13.01%. Calcd. for $C_{18}H_{37}N_5O_9 \cdot H_2CO_3$: C 43.09; H 7.42; N 13.23%.

EXAMPLE 3

(a) Preparation of 6′-N-benzyloxycarbonylkanamycin B 500 mg of kanamycin B (Free base) was suspended in 20 ml of dimethylsulfoxide and 0.76 g of zinc acetate dihydrate was added to the suspension. The mixture was stirred at ambient temperature until it formed a homogeneous solution. To the solution containing a kanamycin B-zinc cation complex as formed was added 280 mg of N-benzyloxycarbonylsuccinimide, and the admixture was allowed to stand overnight at room temperature to effect the N-benzyloxycarbonylation. The resulting reaction solution was poured in small portions into a large volume of ethyl ether and the supernatant was decanted off, followed by washing the lower syrupy phase with ethyl ether and drying to give a syrup. The syrup was charged in a column of CM-Sephadex C-25 ($NH_4^+$ form) which had been impregnated with water-dioxane (1:1). The column was washed with water-dioxane (1:1) and then subjected to gradient elution with solvent mixtures of 0→0.15 N aqueous ammonia/-dioxane (1:1). The fractions containing the desired product was combined together and evaporated to dryness to give 603 mg (90%) of the title compound in the form of its hemicarbonate. $[\alpha]_D^{25} = +109°$ (c=1 in water).

Elemental Analysis

Found: C 48.84; H 6.94; N 10.50%. Calcd. for $C_{26}H_{43}N_5O_{12} \cdot \frac{1}{2}H_2CO_3$: C 49.07; H 6.84; N 10.80%.

(b) Preparation of 6′-N-benzyloxycarbonyl-1,3,2′,3″-tetra-N-tosylkanamycin B 1.01 g of the hemicarbonate product obtained in the step (a) above of this Example 3 and 0.693 g of anhydrous sodium carbonate were added to 20 ml of a mixture of water-dioxane (1:1), followed by addition of 1.36 g of p-toluenesulfonyl chloride under stirring. The admixture obtained was continued to be stirred at 5° C. for further two hours to perform the tetra-N-tosylation, followed by concentration of the reaction solution to a small volume. The concentrate was admixed with water to precipitate a solid, which was washed with ethyl ether and dried to give 1.93 g of a solid. The solid was purified by column chromatography on silica gel using a developing solvent of chloroform-ethanol (10:1) to yield 1.39 g (72%) of a colorless solid of the title compound. $[\alpha]_D^{25} = +19°$ (c=1 in dimethylformamide).

Elemental Analysis

Found: C51.86; H 5.29; N 5.35; S 10.18%. Calcd. for $C_{54}H_{67}N_5O_{26}S_4 \cdot H_2O$: C 51.79; H 5.55; N 5.59; S 10.24%.

(c) Preparation of 6′-N-benzyloxycarbonyl-4″,6″—O—cyclohexylidene-1,3,2′,3″-tetra-N-tosylkanamycin B 1.00 g of the product obtained in the step (b) above of this Example 3 was dissolved in 10 ml of dimethylformamide, to which were then added a catalytic quantity (28 mg) of p-toluenesulfonic acid and 0.13 ml of 1,1-dimethoxycyclohexane. The mixture was agitated at a temperature of 50° C. and a reduced pressure of 35 mmHg for one hour to effect the 4″,6″-O-cyclohexylidenation. Thereafter, the reaction solution was admixed with 1.3 ml of 5% aqueous sodium bicarbonate and concentrated to a syrup. To the latter was added water to form a precipitate, which was removed by filtration and dried to afford 1.08 g of a solid. The solid was purified by column chromatography on silica gel using a developing solvent of ethyl acetate-benzene (3:1) to give 986 mg (92%) of a colorless solid of the title compound. $[\alpha]_D^{25} = +3°$ (c=1 in chloroform).

Elemental Analysis

Found: C 54.62; H 5.66; N 5.26; S 9.68%. Calcd. for $C_{60}H_{75}N_5O_{20}S_4$: C 54.82; H 5.75; N 5.33; S 9.76%.

(d) Preparation of 6′-N:4′-0-carbonyl-4″,6″-O-cyclohexylidene-1,3,2′,3″-tetra-N-tosylkanamycin B 1.77 g of the product from the step (c) above of this Example 3 was dissolved in 35 ml of dimethylformamide, and the solution was ice-cooled, followed by addition thereto of 581 mg of 50% sodium hydride in oil. After stirring for two hours, the mixture was further stirred overnight at ambient temperature to effect the formation of the 4′,6′-cyclic carbamate derivative. The reaction mixture was then admixed with 0.69 ml of acetic acid and evaporated to leave a solid. The solid was washed with water, dried and reprecipitated from acetone-ethyl ether to yield 1.42 g (89%) of a pale brown solid of the title compound. $[\alpha]_D^{25} = -23°$ (c=1 in dimethylformamide).

Elemental Analysis

Found: C 52.50; H 5.53; N 5.79; S 10.45%. Calcd. for $C_{53}H_{67}N_5O_{19}S_4$: C 52.78; H 5.60; N 5.81; S 10.63%.

(e) Preparation of 3′-O-benzylsulfonyl- and 3′,2″-di-O-benzylsulfonyl-6′-N:4′-O-carbonyl-4″,6″-O-cyclohexylidene-1,3,2′,3″-tetra-N-tosylkanamycin B 107 mg of the product from the step (d) above of this Example 3 was dissolved in 2 ml of dry pyridine, and the solution obtained was cooled to −20° C., after which 34 mg of benzylsulfonyl chloride was added to the solution. The resultant mixture was allowed to stand at −20° C. for two hours, when the main reaction, 3′-mono-O-benzylsulfonylation took place with accompanying the 3′,2″-di-O-benzylsulfonylation to an extent. The reaction solution was admixed with 0.02 ml of water and evaporated to leave a syrup, which was then taken up in chloroform to give 20 ml of the solution in chloroform. The chloroform solution was washed with 5% aqueous sodium bicarbonate and then with water and further concentrated to dryness to afford 134 mg of a solid. The solid was purified by column chromatography on silica gel developing with a mixed solvent of chloroform-methyl ethyl ketone (1:2) to yield 92.9 mg (77%) of the 3'-mono-O-benzylsulfonyl compound and 9.8 mg (7%) of the 3',2''-di-O-benzylsulfonyl compound, respectively, both in the form of colorless solid.

(A) The 3'-O-benzylsulfonyl compound: $[\alpha]_D^{25} = -38°$ (c=1 in dimethylformamide). Rf=0.4 with silica gel thin-layer chromatogram with chloroform-acetone (2:3) as developer.

Elemental Analysis

Found: C 52.12; H 5.27; N 4.94; S 11.39%. Calcd. for $C_{60}H_{73}N_5O_{21}S_5 \cdot H_2O$: C 52.27; H 5.48; N 5.08; S 11.63%.

(B) The 3',2''-di-O-benzylsulfonyl compound: $[\alpha]_D^{25} = -52°$ (c=1 in chloroform). Rf=0.7 with the system described in (A) above.

Elemental Analysis

Found: C 53.01; H 5.17; N 4.78; S 12.40%. Calcd. for $C_{67}H_{79}N_5O_{23}S_6$: C53.13; H 5.26; N 4.62; S 12.70%.

EXAMPLE 4

Synthesis of tobramycin (a) Production of 6'-N:4'-O-carbonyl-4'',6''-O-cyclohexylidene-3'-deoxy-3'-iodo-1,3,2',3''-tetra-N-tosylkanamycin B 471 mg of the 3'-mono-O-benzylsulfonyl compound obtained in the above Example 3(e) was dissolved in 9.4 ml of dimethylformamide and 4.7 g of sodium iodide was added to the solution. The mixture was continuously stirred at 100° C. for 2 hours to effect the 3'-iodination. The resultant reaction solution was subsequently treated in the same manner as in the above Example 2(a)(i) to give 203 mg of a solid. The solid was purified by column chromatography on silica gel developing with a solvent of chloroform-methyl ethyl ketone (1:2) to yield 161 mg (79%) of a colorless solid of the title compound. $[\alpha]_D^{25} = -32°$ (c=1 in dimethylformamide).

Elemental Analysis

Found: C 47.92; H 4.93; N 5.31%. Calcd. for $C_{53}H_{66}N_5O_{18}S_4I \cdot H_2O$: C 47.71; H 5.14; N 5.25%.

(b) Production of 6'-N:4'-O-carbonyl-4'',6''-O-cyclohexylidene-3'-deoxy-1,3,2',3''-tetra-N-tosylkanamycin B 145 mg of the product obtained in the above step (a) of this Example 4 was dissolved in 2.9 ml of dry dioxane, to which was added 0.29 ml of tri-n-butyltin hydride followed by addition of 14.5 mg of $\alpha,\alpha'$-azobisisobutyronitrile. The mixture was allowed to stand at 80° C. under nitrogen atmosphere for 30 minutes to effect the reductive replacement of the 3'-iodo group by hydrogen. Concentration of the reaction solution gave a syrup, which was admixed with a volume of ethyl ether to precipitate a solid. The solid was washed with ethyl ether and dried to afford 127 mg (97%) of the title compound as a colorless solid. $[\alpha]_D^{25} = -20°$ (c=0.5 in dimethylformamide).

Elemental Analysis

Found: C 53.70; H 5.65; N 5.66; S 10.47%. Calcd. for $C_{53}H_{67}N_5O_{18}S_4$: C 53.48; H 5.67; N 5.88; S 10.77%.

(c) Production of 3'-deoxykanamycin B (tobramycin)

(i) 104 mg of the product obtained in the step (b) above of the Example 4 was dissolved in 5 ml of liquid ammonia at −50° C., about 150 mg of metallic sodium was added to the solution in liquid ammonia and the mixture was stirred at −50° C. for one hour to effect the removal of the N-tosyl groups. The subsequent distillation off of ammonia was carried out in the same way as in the above Example 2(c) to give the residue comprising the de-tosylated product. This residue was dissolved in water and then heated at 80° C. for one hour to effect the ring-fission of the 4',6'-cyclic carbamate. The reaction solution so obtained was admixed with 3 g of a strongly acidic ion-exchange resin, Dowex 50W×2(H+ form) for neutralization to remove the 4'',6''-O-cyclohexylidene group. The subsequent treatment of the resin and purification of the crude product of 3'-deoxykanamycin B obtained by the same procedure as described in the above Example 2(c) gave 26.0 mg (56%) of 3'-deoxykanamycin B monocarbonate as a colorless solid.

Elemental Analysis

Found: C 42.70; H 7.53; N 13.46%. Calcd. for $C_{18}H_{37}N_5O_9 \cdot 1H_2CO_3$: C 43.09; H 7.42; N 13.23%.

(ii) 300 mg of the 3'-iodo product obtained in the above Example 4(a) was immediately dissolved in 10 ml of liquid ammonia at −50° C., followed by addition of 50 mg of metallic sodium and stirring at −50° C. for 1 hour to effect the reductive replacement of the 3'-iodo group by hydrogen concurrently with the removal of the N-tosyl groups. The subsequent fission of the 4',6'-cyclic carbamate ring, removal of the 4'',6''-O-cyclohexylidene group and purification were carried out following the procedure as described in the step (c)(i) above of this Example 4 to yield 76.3 mg (2%) of 3'-deoxykanamycin B monocarbonate.

EXAMPLE 5

Synthesis of tobramycin (a) Preparation of 2''-O-benzylsulfonyl-6'-N:4'-O—carbonyl-3'-chloro-4'',6''-O-cyclohexylidene-3'-deoxy-1,3,2',3''-tetra-N-tosylkanamycin B 50.0 mg of the 3',2''-di-O-benzylsulfonyl compound obtained in the above Example 3(e) was dissolved in 0.8 ml of dimethylformamide, 14.0 mg of lithium chloride was added to the resultant solution, and the mixture was stirred at 120° C. for 1.5 hours to effect the 3'-chlorination. The reaction solution was then concentrated and subjected to azeotropic distillation with xylene to give a syrupy residue, which was suspended in 10 ml of chloroform. The suspension was washed with water, concentrated to dryness and dried to afford 42.0 mg of a solid. The solid was purified by column chromatography on silica gel using a developing solvent of chloroform-methyl ethyl ketone (1:1) to yield 23.9 mg (53%) of a colorless solid of the title compound. $[\alpha]_D^{25} = -43°$ (c=1 in chloroform).

Elmental Analysis

Found: C 52.36; H 5.32; N 4.89%. Calcd. for $C_{60}H_{72}N_5O_{20}S_5Cl$: C 52.26; H 5.26; N 5.08%.

(b) Production of 3'-deoxykanamycin B 51.5 mg of the product from the step (a) above of this Example 5 was treated with metallic sodium in liquid ammonia by the same procedure as described in the above Example 4(c)(i) to effect concurrently the removal of the N-tosyl group, reduction of the 3'-chloro group and removal of the 2''-O-benzylsulfonyl group. Further, the fission of the 4',6'-cyclic carbamate ring and the removal of the 4'',6''-O-cyclohexylidene group were performed by the procedure similar to that described in Example 4(c)(i). There was thus obtained 12.2 mg (66%) of 3'-deoxykanamycin B monocarbonate.

EXAMPLE 6

Production of 3'-deoxykanamycin (tobramycin)

287 mg of 6'-N:4'-O-carbonyl-4'',6''-O-cyclohexylidene-1,3,2',3''-tetra-N-tosylkanamycin B prepared as in the above Example 3(d) was reacted with 110 mg of benzylsulfonyl chloride in the same manner as described in Example 3(e) to form 328 mg of the mixed benzylsulfonylation products, which were then dissolved in 6 ml of dimethylformamide. The resultant solution was admixed with 102 mg of lithium chloride, and the admixture was stirred at 120° C. for one hour to effect the 3'-chlorination. The subsequent treatment as in the above Example 5(a) gave 300 mg of a solid, which was then treated and purified as described in the above Example 4(c). There was thus obtained 66.6 mg of 3'-deoxykanamycin B monocarbonate. Yield 53% (as calculated from the mixed benzylsulfonylated product employed).

EXAMPLE 7

(a) Preparation of 6'-N:4'-O-carbonyl-4'',6''-O-cyclohexylidene-1,3,2',3''-tetra-N-tosyl-3'-O-tosylkanamycin B 611 mg of 6'-N:4'-O-carbonyl-4'',6''-O-cyclohexylidene-1,3,2',3''-tetra-N-tosylkanamycin B, namely the product obtained in the above Example 3(d) was dissolved in 12 ml of dry pyridine, to which was then added 880 mg of tosyl chloride and the mixture was allowed to stand at 50° C. for 24 hours to effect the 3'-O-tosylation. The subsequent after-treatment and purification by the procedure as described in the above Example 3(e) gave 356 mg (52%) of a colorless solid of the title compound. $[\alpha]_D^{25} = -30°(c=1$ in dimethylformamide).

Elemental Analysis

Found: C 51.75; H 5.32; N 5.30; S 11.57%. Calcd. for $C_{60}H_{73}N_5O_{21}S_5$: C 52.97; H 5.41; N 5.15; S 11.78%.

(b) Preparation of 6'-N:4'-O-carbonyl-4'',6''-O-cyclohexylidene-3'-deoxy-3'-iodo-1,3,2',3''-tetra-N-tosylkanamycin B 60.5 mg of the product from the step (a) above of this Example 7 was dissolved in 1.2 ml of dimethylformamide, 606 mg of sodium iodide was added to the resultant solution, and the mixture was stirred at 100° C. for 2 hours to effect the 3'-iodination. The resultant reaction solution was then treated and purified in the same manner as described in Example 2(a)(i) to give 29.9 mg (58%) of a colorless solid of the title compound.

EXAMPLE 8

(a) Preparation of 6'-N:4'-O-carbonyl-4'',6''-O-cyclohexylidene-3'-O-mesyl-1,3,2',3''-tetra-N-tosylkanamycin B 201 mg of the 4',6'-cyclic carbamate product obtained in Example 3(d) was dissolved in 4 ml of dry pyridine and the solution was cooled to −20° C. and then admixed with 0.03 ml of mesyl chloride. The admixture was allowed to stand at ambient temperature overnight to effect the 3'-mono-O-mesylation. The reaction mixture was subsequently treated in the same way as in the above Example 3(e) to give 218 mg of a solid. The solid was purified by column chromatography on silica gel developing with a solvent of chloroform-ethanol (12:1) to yield 114 mg (53%) of a colorless solid of the title compound. $[\alpha]_D^{25} = -25°(c=1$ in dimethylformamide).

Elemental Analysis

Found: C 50.18; H 5.33; N 5.15; S 12.18%. Calcd. for $C_{54}H_{69}N_5O_{21}S_5$: C 50.49; H 5.41; N 5.45; S 12.48%.

(b) Preparation of 6'-N:4'-O-carbonyl-4'',6''-O-cyclohexylidene-3'-deoxy-3'-iodo-1,3,2',3''-tetra-N-tosylkanamycin B 50.0 mg of the product from the step (a) above of this Example 8 was treated with sodium iodide following the procedure as described in the above Example 7(b). The title compound was thus obtained in yield of 25.5 mg (60%) as a colorless solid.

EXAMPLE 9

Synthesis of tobramycin (a) Preparation of 6'-N:4'-O-carbonyl-3'-chloro-4'',6''-O-cyclohexylidene-3'-deoxy-1,3,2',3''-tetra-N-tosylkanamycin B (i) 509 mg of the 3'-mono-O-benzylsulfonyl compound prepared as in the above Example 3(e) was dissolved in 94 ml of dimethylformamide, 159 mg of lithium chloride was added to the resulting solution, and the mixture was agitated at 120° C. for 30 minutes to effect the 3'-chlorination. The reaction solution was concentrated by evaporation and then subjected to azeotropic distillation with xylene to give a syrupy residue, which was then suspended in 90 ml of chloroform. The suspension in chloroform was washed with water, concentrated to dryness and dried to afford 485 mg of a solid.

The solid was purified by silica gel chromatography using a developing solvent of chloroform-methyl ethyl ketone (1:2) to yield 386 mg (84%) of a colorless solid of the title compound. $[\alpha]_D^{25} = -78°$ (c=1 in chloroform).

Elemental Analysis

Found: C 51.69; H 5.31; N 5.71%. Calcd. for $C_{53}H_{66}N_5O_{18}S_4Cl$: C 51.97; H 5.43; N 5.72%.

(ii) The title compound was prepared in a yield of 76.4 mg (83%) from 102 mg of the product obtained in the Example 7(a) by the same procedure as in the step (i) just above.

(iii) The title compound was also prepared in a yield of 16.7 mg (84%) from 20.9 mg of the product obtained in the Example 8(a) by the same procedure as in the step (i) just above, except for the reaction time of 1.5 hours.

(b) Production of 3'-deoxykanamycin B (tobramycin)

204 mg of the product from the step (a) above of this Example 9 was subjected to the treatment with metallic sodium in liquid ammonia for the removal of the N-tosyl groups and the reduction of the 3'-chloro group and then to the deprotection for the fission of the 4',6'-cyclic carbamate ring and the removal of the 4'',6''-O-cyclohexylidene group by the procedures similar to that described in Example 4(c). There was thus obtained 67.6 mg (76%) of 3'-deoxykanamycin B monocarbonate.

What we claim is:

1. A process for the production of 3'-deoxykanamycin B of the formula

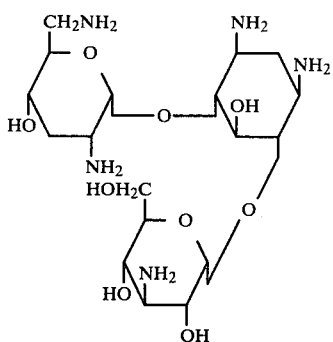

which comprises the steps of:
reacting a 1,3,2',6'-3''-N-protected, 4'',6''-O-protected and 3'-O-sulfonylated derivative of kanamycin B of the general formula (I)

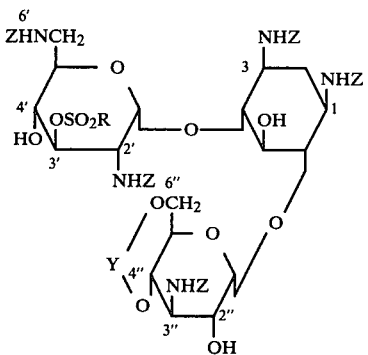

wherein R is an alkyl of 1 to 4 carbon atoms, benzyl or tolyl group, Y is an alkylidene group of 1–6 carbon atoms, a cycloalkylidene group of 3–6 carbon atoms, or tetrahydropyranylidene group as a divalent hydroxyl-protecting group and each Z is tosyl group as the amino-protecting group, with a metal halide of the formula (II)

MX (II)

wherein M is a metal, particularly an alkali metal and X is iodine, chlorine or bromine, in an organic solvent at a temperature of 50°–150° C. for a time of 30 minutes to 2 hours to produce the 3'-halogenated compound of the formula (III)

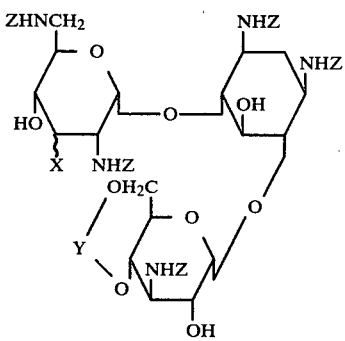

wherein X, Y and Z are as defined above,
reductively dehalogenating the 3'-halo group (X) of the compound (III) to replace the 3'-halo group by hydrogen and to produce the corresponding 3'-deoxykanamycin B compound, and
removing from the latter the remaining amino-protecting groups (Z) and the remaining hydroxyl-protecting group (Y).

2. A process for the production of 3'-deoxykanamycin B, which comprises the steps of:
reacting a 1,3,2',3''-N-protected, 4'',6''-O-protected, 6'-N:4'-O-carbonylated and 3'-O-sulfonylated derivative of kanamycin B of the general formula (IV)

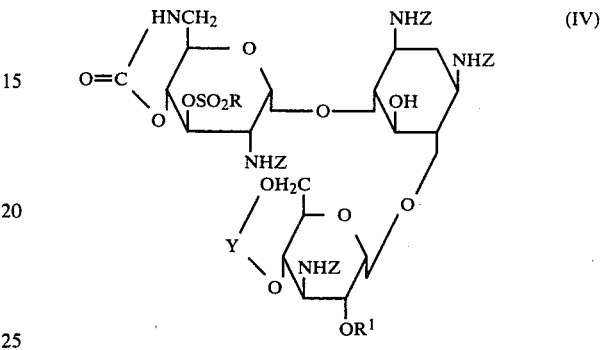

wherein R is an alkyl of 1 to 4 carbon atoms, benzyl or tolyl, group, R¹ is hydrogen or benzylsulfonyl, Y is an alkylidene group of 1–6 carbon atoms, a cycloalkylidene group of 3–6 carbon atoms, or tetrahydropyranylidene group as the divalent hydroxyl-protecting group, and each Z is tosyl as the amino-protecting group, with a metal halide of the formula (II)

MX (II)

wherein M is a metal, particularly an alkali metal and X is iodine, chlorine or bromine, in an organic solvent at a temperature of 50°–150° C. for a time of 30 minutes to 2 hours to produce the 3'-halogenated compound of the formula (V)

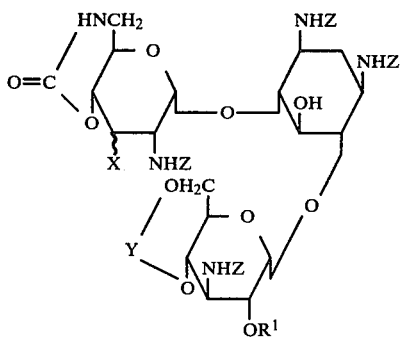

wherein X, Y, Z, and R¹ are as defined above,
reductively dehalogenating the 3'-halo group of the compound (V) to replace the 3'-halo group by hydrogen and to produce the corresponding 3'-deoxykanamycin B compound which is still in the form of the 4',6'-cyclic carbamate, and
fissioning the 4,',6'-cyclic carbamate ring and removing the remaining amino-protecting groups (Z) and the hydroxyl-protecting group (Y) therefrom.

3. The process as claimed in claim 1 or 2 in which the metal halide MX is sodium iodide or lithium chloride.

4. The process as claimed in claim 1 or 2 in which the reduction of the 3'-halo group of the compound (III) or (V) is carried out by reaction with a trialkyltin hydride in the presence of α,α'-azobisisobutyronitrile.

5. The process as claimed in claim 1 or 2 in which the 3'-halo compound (III) or (V) is reacted with metal sodium in liquid ammonia to effect concurrently the reduction of the 3'-halo group (X) into hydrogen and the removal of the amino-protecting arylsulfonyl groups (Z), and the reaction mixture in the liquid ammonia is admixed with methanol and then distilled under reduced pressure to remove the residual ammonia, the residue is dissolved in water and heated to effect the fission of the 4',6'-cyclic carbamate ring which is remaining when the compound (V) is employed, and the resulting solution in water is admixed and neutralized with a strongly acidic cation-exchange resin containing sulfonyl groups to effect the removal of the divalent hydroxyl-protecting group (Y), giving the desired 3'-deoxykanamycin.

6. The 1,3,2,',6',3''-N-sulfonylated, 4'',6''-O-protected and 3'-halogenated kanamycin B derivative of the formula (III)

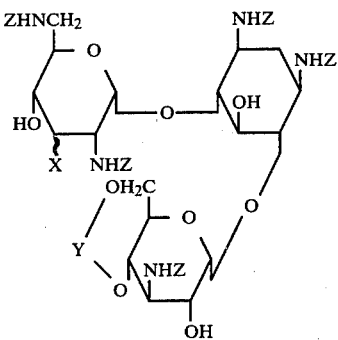

wherein X is a halo group, Y is an alkylidene group of 1~6 carbon atoms, a cycloalkylidene group of 3~6 carbon atoms, or tetrahydropyranylidene group as a divalent hydroxyl-protecting group and each Z is tosyl as the amino-protecting group.

7. The compound of claim 6 which is 4'',6''-O-cyclohexylidene-3'-deoxy-3'-iodo-1,3,2',6',3''-penta-N-tosylkanamycin B.

8. The 1,3,2',3''-N-sulfonylated, 4'',6''-O-protected, 6'-N:4'-O-carbonylated and 3'-halogenated kanamycin B derivative of the formula (V)

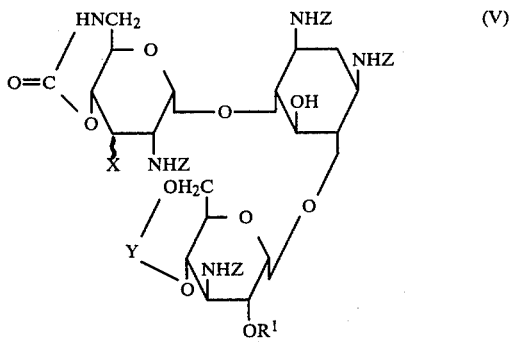

wherein X is a halo group, R¹ is hydrogen or benzylsulfonyl Y is an alkylidene group of 1~6 carbon atoms, a cycloalkylidene group of 3~6 carbon atoms, or tetrahydropyranylidene group as the divalent hydroxyl-protecting group, and each Z is tosyl as the amino-protecting group.

9. The compound of claim 8 which is 6'-N:4'-O-carbonyl-4'',6''-O-cyclohexylidene-3'-deoxy-3'-iodo-1,3,2',3''-tetra-N-tosylkanamycin B;

2''-O-benzylsulfonyl-6'-N:4'-O-carbonyl-3'-chloro-4'',6''-O-cyclohexylidene-3'-deoxy-1,3,2',3''-tetra-N-tosylkanamycin B; and 6'-N:4'-O-carbonyl-3'-chloro-4'',6''-O-cyclohexylidene-3'-deoxy-1,3,2',3''-tetra-N-tosylkanamycin B.

* * * * *